United States Patent
Foxcroft et al.

(10) Patent No.: US 10,695,271 B2
(45) Date of Patent: Jun. 30, 2020

(54) SUN PROTECTIVE COMPOSITIONS

(71) Applicant: Tancream Limited, York (GB)

(72) Inventors: Katy Foxcroft, York (GB); Gillian Robson, York (GB)

(73) Assignee: Tancream Limited, York (GB)

( * ) Notice: Subject to any disclaimer, the term of this patent is extended or adjusted under 35 U.S.C. 154(b) by 0 days.

(21) Appl. No.: 15/777,303

(22) PCT Filed: Apr. 20, 2016

(86) PCT No.: PCT/GB2016/051094
§ 371 (c)(1),
(2) Date: May 18, 2018

(87) PCT Pub. No.: WO2017/085446
PCT Pub. Date: May 26, 2017

(65) Prior Publication Data
US 2018/0263870 A1  Sep. 20, 2018

(30) Foreign Application Priority Data

Nov. 18, 2015 (GB) .................................. 1520301.1

(51) Int. Cl.
| | | |
|---|---|---|
| A61K 8/11 | (2006.01) | |
| A61K 8/35 | (2006.01) | |
| A61K 8/37 | (2006.01) | |
| A61K 8/60 | (2006.01) | |
| A61Q 17/04 | (2006.01) | |
| A61Q 19/04 | (2006.01) | |

(52) U.S. Cl.
CPC .................. *A61K 8/11* (2013.01); *A61K 8/35* (2013.01); *A61K 8/37* (2013.01); *A61K 8/602* (2013.01); *A61Q 17/04* (2013.01); *A61Q 19/04* (2013.01); *A61K 2800/412* (2013.01); *A61K 2800/43* (2013.01); *A61K 2800/48* (2013.01); *A61K 2800/522* (2013.01); *A61K 2800/524* (2013.01); *A61K 2800/592* (2013.01)

(58) Field of Classification Search
CPC . A61K 8/35; A61K 8/37; A61K 8/602; A61K 2800/524; A61K 2800/412; A61Q 17/04; A61Q 19/04
See application file for complete search history.

(56) References Cited

U.S. PATENT DOCUMENTS

| | | | |
|---|---|---|---|
| 5,229,104 A | 7/1993 | Sottery et al. | |
| 6,007,796 A * | 12/1999 | Menzel | A61K 8/14 424/59 |
| 2002/0037261 A1 | 3/2002 | Lapidot et al. | |
| 2003/0039619 A1* | 2/2003 | Bunger | A61K 8/40 424/59 |
| 2008/0025922 A1* | 1/2008 | Marrs | A61K 8/355 424/47 |
| 2010/0209463 A1 | 8/2010 | Pfluecker et al. | |
| 2014/0271752 A1* | 9/2014 | Zeng | A61Q 17/04 424/401 |

FOREIGN PATENT DOCUMENTS

| | | |
|---|---|---|
| WO | 2005032501 A1 | 4/2005 |
| WO | 2010037463 A1 | 4/2010 |
| WO | 2013059167 A2 | 4/2013 |
| WO | 2014132261 A2 | 9/2014 |

OTHER PUBLICATIONS

Friedrich et al., "Easy formulation, demoing ingredients", Personal Care, Mar. 2014. (Year: 2014).*
"The International Search Report and Written Opinion of the International Searching Authority", in connection to PCT/GB2016/051094, filed Apr. 20, 2016, dated Aug. 22, 2016.

* cited by examiner

*Primary Examiner* — Jianfeng Song
(74) *Attorney, Agent, or Firm* — McKee, Voorhees & Sease, PLC

(57) ABSTRACT

There is described a composition comprising one or more UV filtering agents and a sunless tanning system wherein one or both of the UV filtering agent and sunless tanning system is in an encapsulated form.

33 Claims, No Drawings

SUN PROTECTIVE COMPOSITIONS

CROSS-REFERENCE TO RELATED APPLICATIONS

This application claims priority to United Kingdom No. GB 1520301.1, filed Nov. 18, 2015, herein incorporated by reference in its entirety.

FIELD OF THE INVENTION

The present invention relates to a novel formulation comprising a sunless tanning system and a UV filter.

More particularly, the invention relates to a novel formulation comprising a sunless tanning system, such as dihydroxyacetone (1,3-dihydroxypropan-2-one or DHA) and a form of a UV filter with a high SPF factor, e.g. of about 30 or more.

BACKGROUND OF THE INVENTION

Ultraviolet radiation from both sunlight and artificial sources has been divided into three bands (UVA, UVB, and UVC) which emit different quantities of energy UVA radiation is present in the sunlight reaching the earth's surface and has a wavelength of 320 to 400 nanometers (nm.). UVA radiation can cause tanning of the skin but is weak in causing reddening of the skin.

UVB radiation is present in the sunlight reaching the earth's surface and has a wavelength of 290 of 320 nm. UVB causes the sunburn reaction which also stimulates pigmentation (tanning) in the skin.

Ultraviolet energy absorbed by the human skin can produce an erythemal reaction (redness of the skin caused by dilatation and congestion of the capillaries). The intensity of erythemal reaction is generally dependent upon the amount of energy absorbed.

The majority of malignant melanomas are caused by heavy sun exposure in white-skinned populations. Incidence rates of malignant melanomas are highest Australia/New Zealand, where it is the third most common cancer in both males and females. Also, incidence rates are increasing rapidly in many countries, including in the Nordic countries, where the increase has been attributed to excessive sun exposure during holidays at lower latitudes.

According to Cancer Research UK, in 2011 malignant melanoma was the $5^{th}$ most common cancer in the UK, accounting for 4% of all new cases. In males and females separately, malignant melanoma was the $6^{th}$ most common cancer (4% each of the male and female total). In 2011, this amounted to 13,348 new cases of malignant melanoma in the UK. In England and Wales there are about 2,000 deaths each from melanoma and in 2012 there were around 55,500 deaths from melanoma worldwide.

Also, malignant melanoma incidence has an unusual age related pattern when compared with most other cancers. In the UK between 2009 and 2011, an average of 27% of cases was diagnosed in those aged under 50 years.

Malignant melanoma incidence rates have increased overall in Great Britain since the mid-1970s. For males, incidence rates were almost seven times higher in 2009-2011 than in 1975-1977. For females, the increase is smaller but rates have still quadrupled between 1975-1977 and 2009-2011. Since the mid-1970s in Great Britain, malignant melanoma incidence rates have increased more rapidly than any of the current ten most common cancers in males and females.

Most of this increase is attributed to changes in sun-related behaviour such as an increase in frequency of holidays abroad over time. A study published in December 2011 estimated that around 86% of malignant melanomas in the UK in 2010 were linked to exposure to UVR from the sun and sunbeds.

However, some studies have shown that the use of sunscreen does not necessarily reduce the risk of malignant melanoma, because consumers reported that sunscreen use enabled them to spend more time sunbathing and/or because the subjects would still strive to achieve a sun tan, often because a tan is viewed by the consumer as being healthy.

Therefore, there is a need for a formulation that will allow a consumer to have the appearance of a healthy tan, whilst protecting the skin from the undesirable effects of ultraviolet light. Such a composition would comprise a UV filter and a sunless tanning system.

Attempts have been made to provide such a composition comprising a UV filter and DHA, which is considered the most effective sunless tanning system.

One disadvantage of the use of a sunless tanning system, such as DHA is that the appearance of a self-tan can confuse the user into many into thinking that they have a base tan and that they can then sit in the sun without getting burned. However, it is well understood that sunless tanners alone provide only a minimal amount of sun protection.

However, even if a sunless tanning system is combined with a UV filter, the sun-protective abilities generally do not last longer than a few hours, whereas the self-tan may last for as much as about 7-10 days.

It is known to combine a sunless tanning system with a UV filter, but the two interact and the effectiveness of the UV filter can be diminished. A sunless tanning system, such as DHA, provides its optimum effect at a pH of about 3 to 4. However, most UV filters comprise an organic ester, which has the potential to hydrolyse at low pH. Furthermore, DHA is incompatible with mineral UV filters, such as titanium dioxide.

US Patent application No. 2010/0303745 attempts to address the problem of the interaction of the UV filter and the sunless tanning system by using a UV filter with a high SPF. U.S. '745 describes a composition having a sunblock and tanning effect containing dihydroxyacetone and a broad spectrum UV filter having a high SPF of at least about 25.

European Patent application No. 2194958 describes the problem of the interaction of the UV filter and the sunless tanning system by the inclusion of a photostabiliser, such as, a copolymer of adipic acid and neopentyl glycol, to allow the sunscreen agent to remain photostable when subjected to said UV radiation and maintain a portion of the characteristic of UV radiation absorbance.

Therefore, there is a need for an improved formulation which provides UV protection for the skin, whilst providing the consumer with the appearance of a sunless tan. In particular, there is a need for a formulation that comprises a sunless tanning system component and a UV filter component, which prevents or hinders the interaction between the two components.

SUMMARY OF THE INVENTION

Thus, according to a first aspect of the invention there is provided a composition comprising one or more UV filtering agents and a sunless tanning system wherein one or both of the UV filtering agent and sunless tanning system is in an encapsulated form.

In one aspect of the invention the UV filtering agent is in encapsulated form and the sunless tanning system is unencapsulated. In another aspect of the invention the sunless tanning system is in encapsulated form and the UV filtering agent is unencapsulated. In another aspect of the invention each of the UV filtering agent and the sunless tanning system are encapsulated. When each of the UV filtering agent and the sunless tanning system are encapsulated, they may be encapsulated separately or together, i.e. both components in a one microcapsule.

The UV filtering agent or sunscreen agent will generally absorb, filter, and/or block both UVA radiation as well as UVB radiation. The UVB portion encompasses 280-320 nm and the UVA portion encompasses 320-400 nm. Suitable UV filtering agents or sunscreen agents include, but shall not be limited to, benzophenone-3 (2-hydroxy-4-methoxy-benzophenone); benzophenone-4 (5-benzoyl-4-hydroxy-2-methoxybenzenesulfonic acid); benzophenone-5; 3-benzylidene camphor; benzylidene camphor sulfonic acid; bis-ethylhexyloxyphenol methoxyphenyl triazine (BEMT) (bemotrizinol); butyl methoxydibenzoylmethane (avobenzone); camphor benzalkonium methosulfate; diethylamino hydroxybenzoyl hexyl benzoate (DHHB); diethylhexyl butamido triazone; disodium phenyl dibenzylimidazole tetrasulfonate (DPDT); drometrizole trisiloxane; ethylhexyl dimethyl PABA; ethylhexyl methoxycinnamate; ethylhexyl salicylate (octisalate); ethylhexyl triazone; homosalate (3,3,5-trimethylcyclohexyl 2-hydroxybenzoate); isoamyl p-methoxycinnamate; methyl anthranilate (methyl 2-aminobenzoate); 4-methylbenzylidene camphor; methylene bis benzotriazolyl tetramethylbutylphenol (MBBT) (bisoctrizole); octocrylene; octyl methoxycinnamate (octinoxate); phenyl benzimidazole sulfonic acid; polysilicone-15; phenyl dibenzimidazole tetrasulfonate (2-phenylbenzimididazole-5-sulfonic acid); PEG-25 PABA; polyacrylamidomethyl benzylidene camphor; polysilicone-15 (dimethicodiethylbenzalmalonate); terephthalylidene dicamphor sulfonic acid (ecamsule); titanium dioxide; and zinc oxide; and combinations thereof. Where possible the INCI (International Nomenclature of Cosmetic Ingredients) is used. It is especially desirable to encapsulate those UV filtering agents that are susceptible to de-esterication at low pH.

Alternatively, proprietary UV filtering agents may be used. Such proprietary UV filtering agents may comprise an encapsulated pre-solubilised mixture of UV filters (20% w/w octyl methoxycinnamate (ethylhexyl methoxycinnamate), 10% w/w octocrylene and 20% w/w butyl methoxydibenzoylmethane). Such proprietary UV filtering agents provide a very broad spectrum protection covering the whole UVB and UVA range whilst it is easily dispersed in the water phase.

UV filtering agents or sunscreen agents protect against sunburn by absorbing or filtering UVA/UVB from sunlight before it penetrates a person's skin. The degree of protection by a sunscreen is described by the sun protection factor (SPF). The SPF of the UV filtering agents or sunscreen agent used in the formulation of the present invention may vary and may be from about to 2 to about 100, or from about to 5 to about 50, or from about 10 to about 50, or from about 15 to about 50, or from about 20 to about 50, or from about 25 to about 50, or from about 30 to about 50, or from about 35 to about 50, or from about 40 to about 50, or from about 45 to about 50. Preferably, the SPF of the UV filtering agents or sunscreen agent is as high as possible, i.e. ≥25, preferably ≥35, more preferably ≥45 and especially ≥50 or up to 100. The UVA/UVB ratio is used to describe the ratio of UVA to UVB protection offered by UV filtering agents or sunscreen agents. In the present invention the UV filtering agents or sunscreen agent preferably has a UVA/UVB ratio of from 0.2 to 1.

In one embodiment of the present invention, the sunscreen agent is present in an amount of from about 0.5% w/w to about 25% w/w, or from about 0.5% w/w to about 20% w/w, or from about 0.5% w/w to about 10% w/w.

Sunless tanning systems are known to the person skilled in the art. Such sunless tanning systems include, but shall not be limited to, dihydroxyacetone, melanin, mahakanni (*Eclipta alba*), methyl glyoxal, erythrulose, alloxan, 2,3-dihydroxysuccindialdehyde; lawsone (2-hydroxy-1,4-naphthoquinone); raspberry ketone (4-(4-hydroxyphenyl)butan-2-one); chasteberry; and combinations thereof. However, in a preferred aspect of the invention the sunless tanning system is dihydroxyacetone (DHA).

In another embodiment of the present invention, the sunless tanning system, e.g. DHA, is present in an amount of from about 1% w/w to about 20% w/w, preferably from about 1% w/w to about 15% w/w and preferably about 1% w/w to about 5% w/w.

The encapsulated form of the UV filter and/or the sunless tanning system will generally comprise a UV filter and/or sunless tanning system encapsulated in microcapsules or microspheres. Microcapsules or microspheres generally consist of spherical particles 2 millimetres or less in diameter, usually 500 microns or less in diameter. If the particles are less than 1 micron, they are often referred to as nanocapsules or nanospheres. Microcapsules are generally considered to comprise a UV filter and/or sunless tanning system formed into a central core surrounded by an encapsulating structure. Microspheres are generally considered to comprise a sunless tanning system dispersed throughout the particle.

Examples of microcapsules or microspheres include, but shall not be limited to, liposomes; yeast cells; exine shells, i.e. plant pollens or spores; polymeric shells, i.e. polymeric microcapsules or polymeric microspheres; and the like. Microcapsules are known, inter alia, from International patent application Nos. WO 01/49817, WO 2008/071649 and WO 2003/066209; and European patent application No. 0 457 154, which are incorporated herein by reference. It will be understood that the UV filter and/or sunless tanning system may optionally comprise an encapsulated form combined with an immediate release form.

The encapsulation may be by phospholipids, but it will be understood by the person skilled in the art that other means of encapsulation may be used. When the encapsulation is by phospholipids, the carrier may be water/1,3-butylene glycol.

When the UV filter is encapsulated, the composition may comprise up to 25% w/w of the UV filter component in encapsulated form. For the avoidance of doubt, 25% w/w of the UV filter component in encapsulated form will generally comprise 12.5% w/w of the UV filter and 12.5% w/w of emulsion, i.e. the UV filter and the emulsion being in an approximately 1:1 ratio.

The formulation may optionally include a free radical scavenger such as an anti-oxidant. A preferred free radical scavenger is a tri(hydroxyalkyl)rutoside, especially troxerutin. The use of an anti-oxidant may be advantageous in that, inter alia, it can speed up the tanning action of a tanning agent, such as DHA.

Furthermore, troxerutin increases the effect of DHA and is a free radical scavenger, with anti-ageing and anti-inflammatory properties. Troxerutin is also known to have beneficial effects on venous health, for example, troxerutin is used in the treatment of varicose veins.

According to the present invention the sunless tanning system is in encapsulated form, e.g. it may be encapsulated. However, it is within the scope of the present invention for the one or more UV filtering agents to be in free form or encapsulated form, e.g. may be encapsulated. When the UV filtering agents is in encapsulated form they may be encapsulated separately from the sunless tanning system or it may be co-encapsulated with the sunless tanning system.

The sunless tanning/sunscreen composition of the present invention may also include at least one colouring agent. Colouring agents include, but are not limited to, caramel, melanin, extracts from various botanicals, oxides of iron, zinc, and/or titanium, dyes, combinations of the foregoing, and the like. When used, the amount of colouring agent in the composition of the present invention is from about 0.1% w/w to about 1.0% w/w. However, the present invention is not limited in this regard as other weight percentages can also be employed.

A preferred colouring agent is a bronzer. Bronzer compositions add colour to the skin to provide a cosmetic benefit, such as better, healthier skin colour. Bronzers may also be advantageously used to aid in the application of the composition comprising the one or more UV filtering agents. They provide a visual aid to the user to prevent uneven administration on the skin surface and an immediate darkening effect on the skin. A bronzer may comprise a water-soluble dye. Examples of such water soluble dyes include, but shall not be limited to, caramel, carmine, fluorescein derivatives, methoxsalen, trioxsalen, carbon black, azo dyes, anthraquinone dyes, blue azulenes, guajazulene, chamuzulene, erythrosin, bengal rose, phloxin, cyanosin, daphinin, eosin G, cosin 1OB, Acid Red 51, Red Dye 4, Red Dye 40, Blue Dye 1, Yellow Dye 5, Red Dye 4, Orange Dye 4, Ext. Violet Dye 2, and Ext. Yellow Dye 10. Other dyes are listed on page 1628-30 of the International Cosmetic Ingredient Dictionary and Handbook, eds. Wenninger and McEwen (The Cosmetic, Toiletry, and Fragrance Assoc, Washington, D.C., 7th Edition, 1997) (hereinafter "ICT Handbook"), the contents of which are incorporated herein by reference.

The composition may further include one or more skin conditioners. Skin conditioners that may be used include, but are not limited to, emollients, emulsifier, humectants, film forming agents, thickeners, preservatives, pH adjusters, fragrances, etc.

Emollients soften the skin surface and also control a rate of evaporation of the sunless tanning/sunscreen composition from the skin surface. Suitable emollients include, but are not limited to, cocoglycerides, cyclomethicone, dimethicone, dicapryl maleate, caprylic/capric triglyceride, isopropyl myristate, octyl stearate, isostearyl linoleate, lanolin oil, coconut oil, cocoa butter, shea butter, olive oil, avocado oil, aloe extracts, jojoba oil, castor oil, fatty acids such as oleic acid and stearic acid, fatty alcohols such as cetyl alcohol and hexadecyl alcohol, diisopropyl adipate, hydroxybenzoate ester, benzoic acid esters of C9-C15 alcohols, isononyl iso-nonanoate, alkanes such as mineral oil, silicones such as dimethyl polysiloxane, ether such as polyoxypropylene butyl ether and polyoxypropylene cetyl ether, C12-C15 alkyl benzoate, and combinations thereof. In the composition of the present invention, the total amount of emollient may be in the range of from about 0.25% w/w to about 30% w/w.

Various emulsifying agents may be included in the sunless tanning/sunscreen composition of the present invention to provide suitable rheological characteristics to the sunless tanning/sunscreen composition. Such emulsifying agents include, but are not limited to, cetyl alcohol, stearyl alcohol, combinations of the foregoing, and the like. Particular emulsifiers which may be mentioned are non-ionic emulsifiers, such as polyglyceryl-6 stearate, polyglyceryl-6 behenate, and the like, which are generally available under the name Tego® Care from Evonik Industries AG. The emulsifying agent used in the composition of the invention may be non-ionic, anionic or cationic, but preferably a cationic emulsifying agent is used.

In the present invention, the amount of emulsifying agent may be from about 0.01% w/w to about 10% w/w.

Humectants can be included in the sunless tanning/sunscreen composition of the present invention to stabilize the water content, promote water retention, and control evaporation. Suitable humectants include, but are not limited to, glycerin, pentylene glycol, hexylene glycol, propylene glycol, butylene glycol, sorbitol, PEG-4, and combinations thereof. A preferred humectant is glycerin, which when used in the sunless tanning/sunscreen composition of the present invention is present in an amount from about 1.0% w/w to about 10% w/w.

A film forming agent may optionally be included in the composition of the present invention, as it can provide water resistant properties to the composition. However, it is also within the scope of the invention for no film forming agent to be present. Generally, the film forming agent is a hydrophobic material that provides a waterproofing effect to the composition when applied on skin. Suitable film forming agents include, but are not limited to, copolymers of acrylates or acrylates/acrylamides, combinations of acrylates and C12-C22 alkylmethacrylate copolymers, poly ethylenes, waxes, esters of polyvinyl pyrrolidone (PVP)/dimethiconylacrylate/polycarbamylpolyglycol, butylated PVP, PVP/hexadecene copolymer, PVP/eicosene copolymer, tricontanyl PVP, combinations of the foregoing, and the like. In the composition of the present invention, film forming agents may be present in an amount of from about 0.1% w/w to about 5% w/w.

Thickeners may also be used in the sunless tanning/sunscreen composition of the present invention and can include synthetic and natural gum or polymer products, polysaccharide thickening agents, associative thickeners, anionic associative rheology modifiers, cationic associative rheology modifiers, nonionic associative rheology modifiers, oil-thickening agents, acrylates/Cio-C3o alkylacrylate crosspolymer, acrylates/aminoacrylates/Cio-C3o alkyl PEG-20 itaconate copolymer, acrylates copolymer, acrylates/steareth-20 methacrylate copolymer, acrylates/beheneth-25 methacrylate copolymer, PEG-150/decyl alcohol/SMDI copolymer, PVP, carbomer, PEG crosspolymer, acrylates/palmeth-25 acrylates copolymer, polysaccharides, polyacrylates, polyether-1, sodium magnesium silicates, sodium carbomers, sodium polyacrylates, sodium polymethacrylates, sodium polyacryloyldimethyl taurates, sodium acryloyldimethyl taurate copolymers, sodium carragenan, sodium carboxymethyl dextran, hydroxyethylcellulose, hydroxypropyl cyclodextran, bentonites, trihydroxystearin, aluminium-magnesium hydroxide stearate, xanthan gum, and any combinations thereof. Preferably, the thickening agent is carbomer, sodium carbomer, xanthan gum, or any combinations thereof. The amount of thickener when used in the sunless tanning/sunscreen composition of the present invention may be from about 0.01% w/w to about 10% w/w.

Gelling agents may also be included in the sunscreen compositions. Examples of suitable hydrophilic gelling agents include carboxyvinyl polymers such as the Carbopol products (carbomers) and the Pemulen products (acrylate/C10-C30-alkylacrylate copolymer); polyacrylamides, for instance the cross-linked copolymers sold under the names Sepigel 305 (CTFA name: polyacrylamide/C13-14 isoparaffin/Laureth 7) or Simulgel 600 (CTFA name: acrylamide/sodium acryloyldimethyltaurate copolymer/isohexadecane/polysorbate 80) by the company SEPPIC; 2-acrylamido-2-methylpropanesulfonic acid polymers and copolymers, which are optionally cross-linked and/or neutralized, for instance the poly(2-acrylamido-2-methylpropanesulfonic acid) (CTFA name: ammonium polyacryldimethyltauramide); cellulose-based derivatives such as hydroxyethylcellulose; polysaccharides and especially gums such as xanthan gum; and mixtures thereof.

In some instances, the gelling agent is ammonium acryloyldimethyltaurate/steareth-25 methacrylate crosspolymer, commercially available from Clariant under the trade name Aristoflex HMS.

Preservatives may also be included in the composition of the present invention to protect the composition from microbial contamination and/or oxidation. Preservatives that may be incorporated into the composition include, but are not limited to, diazolidinyl urea, chloromethylisotiazolinone, methylisothiazolinone, vitamin C, butylated hydroxytoluene (BHT), butylparaben, ethylparaben, methylparaben, propylparaben, isobutylparaben, phenoxyethanol, ethylhexyl glycerine, and combinations thereof. The amount of preservative present in the sunless tanning/sunscreen composition of the present invention is preferably from about 0.01 wt. % to about 2 wt. %. However, the present invention is not limited in this regard as other weight percentages can also be employed.

Materials useful in adjusting the pH of the sunless tanning/sunscreen composition of the present invention may also be included. Such materials include, but are not limited to, sodium hydroxide, triethanolamine, salts of EDTA, and citric acid. Preferably, the composition is adjusted to a pH from about 4.0 to about 7 using a suitable amount of citric acid. As herein described, a sunless tanning system, such as DHA, provides its optimum effect at a pH of about 3 to 4. However, most UV filters comprise an organic ester, which has the potential to hydrolyse at low pH. Furthermore, DHA is incompatible with mineral UV filters, such as titanium dioxide.

Fragrances may also be included in the sunless tanning/sunscreen composition of the present invention. Fragrances are generally aromatic compounds that impart aesthetically pleasing qualities of smell. Materials that can be used to provide fragrance to the sunless tanning/sunscreen composition of the present invention include, but are not limited to, essential oils, extracts of certain flowers (e.g., rose, jasmine, and the like), extracts of certain fruits (e.g., coconut, apple, melon, and the like), alcohols, combinations of the foregoing, and the like. The composition of the present invention typically includes up to about 1.0 wt. % fragrance and preferably from about 0.05 wt. % to about 0.5 wt. %. However, the present invention is not limited in this regard as other weight percentages can also be employed.

The composition of the invention may include additional sunscreen filters such as, for example, mineral UV filters. Examples of mineral UV filters include pigments and nano-pigments (mean size of the primary particles is generally is from 5 nm to 100 nm or from 10 nm to 50 nm) of treated or untreated metal oxides such as, for example, nano-pigments of titanium oxide (amorphous or crystallized in rutile and/or anatase form), of iron oxide, of zinc oxide, of zirconium oxide or of cerium oxide. Such mineral sunscreen filters are generally incompatible with a sunless tanning system, such as, DHA, therefore it is generally desirable that such mineral sunscreen filters are encapsulated as herein described. The treated nano-pigments are pigments that have undergone one or more surface treatments of chemical, electronic, mechanochemical and/or mechanical nature with compounds as described, for example, in Cosmetics & Toiletries, February 1990, Vol. 105, pp. 53-64, such as amino acids, beeswax, fatty acids, fatty alcohols, anionic surfactants, lecithins, sodium, potassium, zinc, iron or aluminium salts of fatty acids, metal (titanium or aluminium) alkoxides, polyethylene, silicones, proteins (collagen or elastin), alkanolamines, silicon oxides, metal oxides, sodium hexametaphosphate, alumina or glycerol.

The composition may be in the form of, but is not limited to, a lotion, spray, gel, cream, foam, or the like, suitable for topical application to a person's skin.

According to a further aspect of the invention there is provided a method of sunless tanning and UV filtering the skin of a person which comprises the application of a composition comprising one or more UV filtering agents and a sunless tanning system wherein one or both of the UV filtering agent and sunless tanning system is in an encapsulated form, as herein described.

What is claimed is:

1. A composition comprising one or more UV filtering agents and a sunless tanning system wherein each of the UV filtering agent and sunless tanning system is in an encapsulated form, wherein the composition does not include an unencapsulated sunless tanning system.

2. The composition according to claim 1 wherein each of the UV filtering agent and the sunless tanning system are encapsulated separately.

3. The composition according to claim 1 wherein each of the UV filtering agent and the sunless tanning system are encapsulated together, i.e. both components are in one microcapsule.

4. The composition according to claim 1 wherein the one or more UV filtering agents are selected from one or more of benzophenone-3 (2-hydroxy-4-methoxy-benzophenone); benzophenone-4 (5-benzoyl-4-hydroxy-2-methoxybenzenesulfonic acid); benzophenone-5; 3-benzylidene camphor; benzylidene camphor sulfonic acid; bis-ethylhexyloxyphenol methoxyphenyl triazine (BEMT) (bemotrizinol); butyl methoxydibenzoylmethane (avobenzone); camphor benzalkonium methosulfate; diethylamino hydroxybenzoyl hexyl benzoate (DHHB); diethylhexyl butamido triazone; disodium phenyl dibenzylimidazole tetrasulfonate (DPDT); drometrizole trisiloxane; ethylhexyl dimethyl PABA; ethylhexyl methoxycinnamate; ethylhexyl salicylate (octisalate); ethylhexyl triazone; homosalate (3,3,5-trimethylcyclohexyl 2-hydroxybenzoate); isoamyl p-methoxycinnamate; methyl anthranilate (methyl 2-aminobenzoate); 4-methylbenzylidene camphor; methylene bis-benzotriazolyl tetramethylbutylphenol (MBBT) (bisoctrizole); octocrylene; octyl methoxycinnamate (octinoxate); phenyl benzimidazole sulfonic acid polysilicone-15; phenyl dibenzimidazole tetrasulfonate (2-phenylbenzimididazole-5 sulfonic acid); PEG-25 PABA; polyacrylamidomethyl benzylidene camphor; polysilicone-15 (dimethicodiethylbenzalmalonate); terephthalylidene dicamphor sulfonic acid (ecamsule); titanium dioxide; and zinc oxide; and combinations thereof.

5. The composition according to claim 1 wherein the UV filtering agents have an SPF of from about to 2 to about 100.

6. The composition according to claim 1 wherein the UV filtering agents have an SPF of ≥25.

7. The composition according to claim 1 wherein the UV filtering agents have a UVA/UVB ratio of 0.2 to 1.

8. The composition according to claim 1 wherein the UV filtering agents are present in an amount of from about 0.5% w/w to about 25% w/w.

9. The composition according to claim 1 wherein the UV filtering agent comprises 20% w/w octyl methoxycinnamate (ethylhexyl methoxycinnamate), 10% w/w octocrylene and 20% w/w butyl methoxydibenzoylmethane.

10. The composition according to claim 1 wherein the sunless tanning system is selected from one or more of dihydroxyacetone; melanin; mahakanni (*Eclipta alba*); methyl glyoxal; erythrulose; alloxan; 2,3-dihydroxysuccidialdehyde; lawsone (2-hydroxy-1,4-naphthoquinone); raspberry ketone (4-(4-hydroxyphenyl)(butan-2-one); chasteberry; and combinations thereof.

11. The composition according to claim 1 wherein the sunless tanning system comprises includes dihydroxyacetone.

12. The composition according to claim 1 wherein the sunless tanning system is present in an amount of from about 1% w/w to about 20% w/w.

13. The composition according to claim 1 wherein the sunless tanning system is encapsulated in microcapsules or microspheres.

14. The composition according to claim 1 wherein the composition includes a free radical scavenger.

15. The composition according to claim 14 wherein the free radical scavenger is a tri(hydroxyalkyl)rutoside.

16. The composition according to claim 13 wherein the free radical scavenger is troxerutin.

17. The composition according to claim 1 wherein the composition includes at least one colouring agent.

18. The composition according to claim 17 wherein the colouring agent is a bronzer.

19. The composition according to claim 18 wherein the bronzer is a water-soluble dye.

20. The composition according to claim 1 wherein the composition includes an emollient.

21. The composition according to claim 1 wherein the composition includes an emulsifier.

22. The composition according to claim 21 wherein the emulsifier is a non-ionic emulsifier.

23. The composition according to claim 21 wherein the emulsifier is an anionic emulsifier.

24. The composition according to claim 21 wherein the emulsifier is a cationic emulsifier.

25. The composition according to claim 22 wherein the non-ionic emulsifier is polyglyceryl-6 stearate or polyglyceryl-6 behenate, and combinations thereof.

26. The composition according to claim 1 wherein the composition includes a humectant.

27. The composition according to claim 1 wherein the composition includes a film forming agent.

28. The composition according to claim 1 wherein the composition includes a thickener.

29. The composition according to claim 1 wherein the composition includes a gelling agent.

30. The composition according to claim 1 wherein the composition includes a preservative.

31. The composition according to claim 1 wherein the composition includes a pH adjuster.

32. The composition according to claim 1 wherein the composition includes a fragrance.

33. The composition according to claim 1 wherein the composition includes an additional sunscreen filter.

* * * * *

UNITED STATES PATENT AND TRADEMARK OFFICE
CERTIFICATE OF CORRECTION

| | | |
|---|---|---|
| PATENT NO. | : 10,695,271 B2 | Page 1 of 1 |
| APPLICATION NO. | : 15/777303 | |
| DATED | : June 30, 2020 | |
| INVENTOR(S) | : Katy Foxcroft and Gillian Robson | |

It is certified that error appears in the above-identified patent and that said Letters Patent is hereby corrected as shown below:

In the Claims

In Column 9, Claim 11, Line 16:
DELETE: "includes"

Signed and Sealed this
Twenty-second Day of September, 2020

Andrei Iancu
*Director of the United States Patent and Trademark Office*